US008647369B2

(12) United States Patent
Gorek et al.

(10) Patent No.: US 8,647,369 B2
(45) Date of Patent: Feb. 11, 2014

(54) MINIMAL PROFILE ANTERIOR BRACKET FOR SPINAL FIXATION

(76) Inventors: Josef E. Gorek, Ross, CA (US); Scott Jones, McMurray, PA (US)

(*) Notice: Subject to any disclaimer, the term of this patent is extended or adjusted under 35 U.S.C. 154(b) by 203 days.

(21) Appl. No.: 13/111,198

(22) Filed: May 19, 2011

(65) Prior Publication Data
US 2011/0288591 A1 Nov. 24, 2011

Related U.S. Application Data

(60) Provisional application No. 61/395,875, filed on May 19, 2010.

(51) Int. Cl.
*A61B 17/70* (2006.01)
*A61B 17/80* (2006.01)

(52) U.S. Cl.
USPC .......................................... 606/246; 606/286

(58) Field of Classification Search
USPC .................. 606/70–71, 280–281, 286, 291, 606/297–298, 246; 623/17.16, 17.11
See application file for complete search history.

(56) References Cited

U.S. PATENT DOCUMENTS

| | | | |
|---|---|---|---|
| 3,741,205 A | 6/1973 | Markolf et al. |
| 4,047,524 A | 9/1977 | Hall |
| 4,434,796 A | 3/1984 | Karapetian et al. |
| 4,456,006 A | 6/1984 | Wevers et al. |
| 4,905,679 A | 3/1990 | Morgan |
| 4,923,471 A | 5/1990 | Morgan |
| 5,085,660 A | 2/1992 | Lin |
| 5,147,361 A | 9/1992 | Ojima et al. |
| 5,180,381 A | 1/1993 | Aust et al. |
| 5,324,290 A | 6/1994 | Zdeblick et al. |
| 5,364,399 A | 11/1994 | Lowery et al. |
| 5,662,655 A | 9/1997 | Laboureau et al. |
| 5,676,666 A | 10/1997 | Oxland et al. |
| 5,681,312 A | 10/1997 | Yuan et al. |
| 5,702,392 A | 12/1997 | Wu et al. |
| 5,713,899 A | 2/1998 | Marnay et al. |

(Continued)

FOREIGN PATENT DOCUMENTS

| | | |
|---|---|---|
| WO | WO 2007/098288 A2 | 8/2007 |
| WO | WO 2009/064644 A1 | 5/2009 |
| WO | WO 2010/017357 A1 | 2/2010 |

OTHER PUBLICATIONS

The PCT/US2011/029171 International Search Report mailed May 26, 2011; 3 pages.

*Primary Examiner* — Nicholas Woodall
*Assistant Examiner* — Larry E Waggle, Jr.
(74) *Attorney, Agent, or Firm* — Carter, DeLuca, Farrell & Schmidt, LLP (57) ABSTRACT

A spinal fixation device for securing to a spine includes a body having one or more longitudinal members extending between a pair of wedge members. Each wedge member defines one or more openings therethrough for the reception of a bone screw. The wedge members are disposed on opposite ends of the one or more longitudinal members. One of the wedge members is positionable within a first intervertebral space and the other wedge member is positionable within a second intervertebral space. The one or more longitudinal members define a length that spans one or more vertebrae. The one or more longitudinal members are positionable within the one or more vertebrae when the wedge members are positioned within the respective first and second intervertebral spaces to maintain the body in a minimal profile orientation relative to the spine.

16 Claims, 5 Drawing Sheets

(56) References Cited

U.S. PATENT DOCUMENTS

| | | |
|---|---|---|
| 5,733,287 A | 3/1998 | Tepic et al. |
| 5,899,904 A | 5/1999 | Errico et al. |
| 5,904,683 A | 5/1999 | Pohndorf et al. |
| 5,941,881 A | 8/1999 | Barnes |
| 6,099,531 A | 8/2000 | Bonutti |
| 6,129,730 A | 10/2000 | Bono et al. |
| 6,159,213 A | 12/2000 | Rogozinski |
| 6,206,881 B1 | 3/2001 | Frigg et al. |
| 6,224,602 B1 | 5/2001 | Hayes |
| 6,228,085 B1 * | 5/2001 | Theken et al. ............... 606/289 |
| 6,254,603 B1 | 7/2001 | Gertzbain et al. |
| 6,273,889 B1 | 8/2001 | Richelsoph |
| 6,306,136 B1 | 10/2001 | Baccelli |
| 6,306,139 B1 | 10/2001 | Fuentes |
| 6,309,393 B1 | 10/2001 | Tepic et al. |
| 6,336,928 B1 | 1/2002 | Guerin et al. |
| 6,432,106 B1 | 8/2002 | Fraser |
| 6,454,769 B2 | 9/2002 | Wagner et al. |
| 6,458,133 B1 | 10/2002 | Lin |
| 6,524,315 B1 | 2/2003 | Selvitelli et al. |
| 6,533,786 B1 | 3/2003 | Needham et al. |
| 6,547,790 B2 | 4/2003 | Harkey, III et al. |
| 6,595,993 B2 | 7/2003 | Donno et al. |
| 6,620,165 B2 | 9/2003 | Wellisz |
| 6,719,759 B2 | 4/2004 | Wagner et al. |
| 6,746,450 B1 | 6/2004 | Wall et al. |
| 6,755,832 B2 | 6/2004 | Happonen et al. |
| 6,884,242 B2 | 4/2005 | LeHuec et al. |
| 6,916,320 B2 | 7/2005 | Michelson |
| 6,932,820 B2 | 8/2005 | Osman |
| 6,969,390 B2 | 11/2005 | Michelson |
| 6,984,234 B2 | 1/2006 | Bray |
| 6,989,012 B2 | 1/2006 | LeHuec et al. |
| 7,001,389 B1 | 2/2006 | Navarro et al. |
| 7,041,105 B2 | 5/2006 | Michelson |
| 7,048,739 B2 | 5/2006 | Michelson |
| 7,232,441 B2 | 6/2007 | Altarac et al. |
| 7,303,563 B2 | 12/2007 | Poyner et al. |
| 7,833,245 B2 * | 11/2010 | Kaes et al. .................... 606/246 |
| 7,875,076 B2 | 1/2011 | Mathieu et al. |
| 2003/0100898 A1 | 5/2003 | Wellisz |
| 2004/0097935 A1 | 5/2004 | Richelsoph et al. |
| 2004/0153078 A1 | 8/2004 | Grinberg |
| 2005/0124994 A1 | 6/2005 | Berger et al. |
| 2005/0240185 A1 | 10/2005 | Boomer et al. |
| 2006/0058796 A1 | 3/2006 | Hartdegen et al. |
| 2006/0074420 A1 * | 4/2006 | LeHuec et al. ................ 606/71 |
| 2006/0155284 A1 | 7/2006 | Doherty et al. |
| 2006/0229610 A1 | 10/2006 | Piehl |
| 2006/0247881 A1 | 11/2006 | De Canniere et al. |
| 2007/0123884 A1 | 5/2007 | Abdou |
| 2007/0233119 A1 | 10/2007 | Markworth |
| 2007/0299441 A1 | 12/2007 | Hoffman et al. |
| 2008/0086124 A1 | 4/2008 | Forton et al. |
| 2008/0086135 A1 * | 4/2008 | White ............................ 606/69 |
| 2008/0177313 A1 | 7/2008 | Lemoine et al. |
| 2008/0234750 A1 | 9/2008 | Woods et al. |
| 2008/0312699 A1 | 12/2008 | Johnson et al. |
| 2010/0057134 A1 * | 3/2010 | Lowry et al. .................. 606/286 |
| 2010/0137916 A1 * | 6/2010 | Hynes et al. .................. 606/280 |

* cited by examiner

MINIMAL PROFILE ANTERIOR BRACKET FOR SPINAL FIXATION

CROSS-REFERENCE TO RELATED APPLICATIONS

This application claims priority to, and the benefit of, U.S. Provisional Patent Application No. 61/395,875, filed on May 19, 2010, the entire contents of which are hereby incorporated by reference herein.

BACKGROUND

1. Technical Field

The present disclosure relates to spinal fixation and, more particularly, to anterior brackets for providing support and stabilization to the spinal column and for inhibiting expulsion of an interbody implant disposed within an intervertebral space.

2. Background of Related Art

The human spinal column is a complex system of bones and connective tissues that provides support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae, and 5 lumbar vertebrae. The lower portion is comprised of the sacral and coccygeal bones. The vertebrae, or vertebral bodies, progressively increase in size from the upper portion downwards to the lower portion.

An intervertebral disc along with two posterior facet joints cushion and dampen the various translational and rotational forces exerted upon the spinal column. The intervertebral discs are spacers located between adjacent vertebral bodies, while the facets provide stability at the posterior portions of adjacent vertebrae.

The spine is a flexible structure capable of a large range of motion. There are various disorders, diseases and types of injury, however, which restrict the range of motion of the spine or interfere with important elements of the nervous system. These include, but are not limited to, scoliosis, kyphosis, excessive lordosis, spondylolisthesis, slipped or ruptured discs, degenerative disc disease, vertebral body fracture, and tumors. Persons suffering from any of the above conditions may experience extreme or debilitating pain and oftentimes experience diminished nerve function.

Spinal fixation apparatuses are widely employed in surgical processes for correcting spinal injuries and diseases. When an intervertebral disc has degenerated to the point of requiring removal, there are a variety of interbody implants that are utilized to take the place of the disc such as PEEK interbody spacers, metal cages and cadaver and human bone implants. In order to facilitate stabilization of these interbody implants, additional implants are commonly employed. For example, longitudinally linked rods may be secured to coupling elements which, in turn, are secured to bone by spinal bone fixation fasteners, e.g., pedicle screws, hooks, etc.

As an alternative to using rods, plate and screw systems may be employed to stabilize and secure the anterior or lateral portion of the spine. In one approach, an interbody implant is placed between the vertebrae and a substantially flat plate is positioned across the intervertebral space and secured to the face of each adjacent vertebral body to inhibit expulsion of the interbody implant. This approach maximizes the fusion graft material that can be placed between the vertebrae, and maximizes the surface area contact between the interbody implant and the adjacent vertebra.

Nonetheless, soft tissue and vasculature limit space for plate and screw systems adjacent the spine. Therefore, there is a continuing need for providing stability to the spine while preventing expulsion of an interbody implant positioned between adjacent vertebrae of the spine without impeding upon soft tissue and vasculature. Currently available on the market are a number of low profile or "zero profile" anterior spinal implants and fixation devices for application to the anterior aspect of the cervical and/or the lumbar spinal segments. Examples include the Synthes "ZeroP" anterior cervical cage and plate combination for use in the cervical spine and the Synthes "SynFix" anterior lumbar cage and plate combination for use in the lumbar spine. However, these and other similarly designed implants are dedicated to use at a single segment. Should the need exist for a low profile implant to be applied at two levels, two of these separate and distinct implants would need to be employed. Thus, it is desirable to have an implant that can span across two or more disc spaces while maintaining the desired advantages associated with a zero profile or low profile relative to the anterior limits of the disc spaces and/or the anterior limits of the vertebral bodies.

SUMMARY

Accordingly, a system for securing a spinal fixation device to a spine is disclosed. The system includes one or more bone screws and a spinal fixation device. The one or more bone screws may be formed of a first material and at least a portion of the spinal fixation device may be formed of a second material. The first and second materials are selected to enhance securement of the one or more bone screws to the spinal fixation device.

The spinal fixation device includes a body having a pair of longitudinal members extending between a pair of wedge members. The body is dimensioned to resist deforming forces including one or both of flexion extension forces and axial compression forces extending through the body.

The pair of wedge members is disposed on opposite ends of the pair of longitudinal members. One of the wedge members is at least partially positionable within a first intervertebral space of the spine and the other wedge member is at least partially positionable within a second intervertebral space of the spine. One or both of the wedge members is at least partially wedge shaped. Each wedge member defines one or more openings therethrough for the reception of one or more bone screws. One or both of the wedge members may define two or more openings therethrough for the passage and reception of a bone screw in each opening. One or more openings are disposed at an angle relative to an anterior surface of the body in order to facilitate the securement of the bone screw to another vertebra adjacent one of the first or second intervertebral spaces.

The pair of longitudinal members defines a length that spans one or more vertebra of the spine. The longitudinal members are positionable within a recess defined within the one or more vertebrae. The pair of longitudinal members is at least partially positionable within the one or more vertebra when the pair of wedge members is positioned within the respective first and second intervertebral spaces to maintain the body in a minimal profile orientation relative to the spine. The one or more longitudinal members may be positioned even with or substantially even with an anterior surface of the one or more vertebrae. Alternatively, the one or more longitudinal members may be recessed below an anterior surface of the one or more vertebrae.

In one aspect, a method of securing a spinal fixation device to an anterior portion of a spine includes providing a spinal fixation device having a body including one or more longitudinal members extending between a pair of wedge members. The method involves forming one or more recesses within one or more vertebrae of the spine, positioning the one or more longitudinal members at least partially within the one or more recesses, positioning one of the wedge members at least partially in a first intervertebral space of the spine, positioning the other wedge member at least partially in a second intervertebral space of the spine, and securing the spinal fixation device to the anterior portion of the spine so that the spinal fixation device is in a minimal profile orientation relative to the anterior portion of the spine.

The method may include forming the one or more recesses along a plurality of contiguous vertebrae of the spine and positioning the one or more longitudinal members at least partially within the one or more recesses along each of the plurality of contiguous vertebrae. One part of the procedure may include securing each wedge member to a second vertebra of the spine with one or more bone screws, the second vertebra being adjacent the one or more vertebrae. The method may involve spanning the one or more longitudinal members along a plurality of vertebrae. One part of the procedure may include positioning the one or more longitudinal members within the one or more recesses in a zero profile orientation relative to the anterior portion of the spine. The method may involve positioning the one or more longitudinal members within the one or more recesses in a low profile orientation relative to the anterior portion of the spine.

BRIEF DESCRIPTION OF THE DRAWINGS

Embodiments of the present disclosure are described herein with reference to the accompanying drawings, wherein.

DETAILED DESCRIPTION

Various embodiments of the present disclosure will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1:
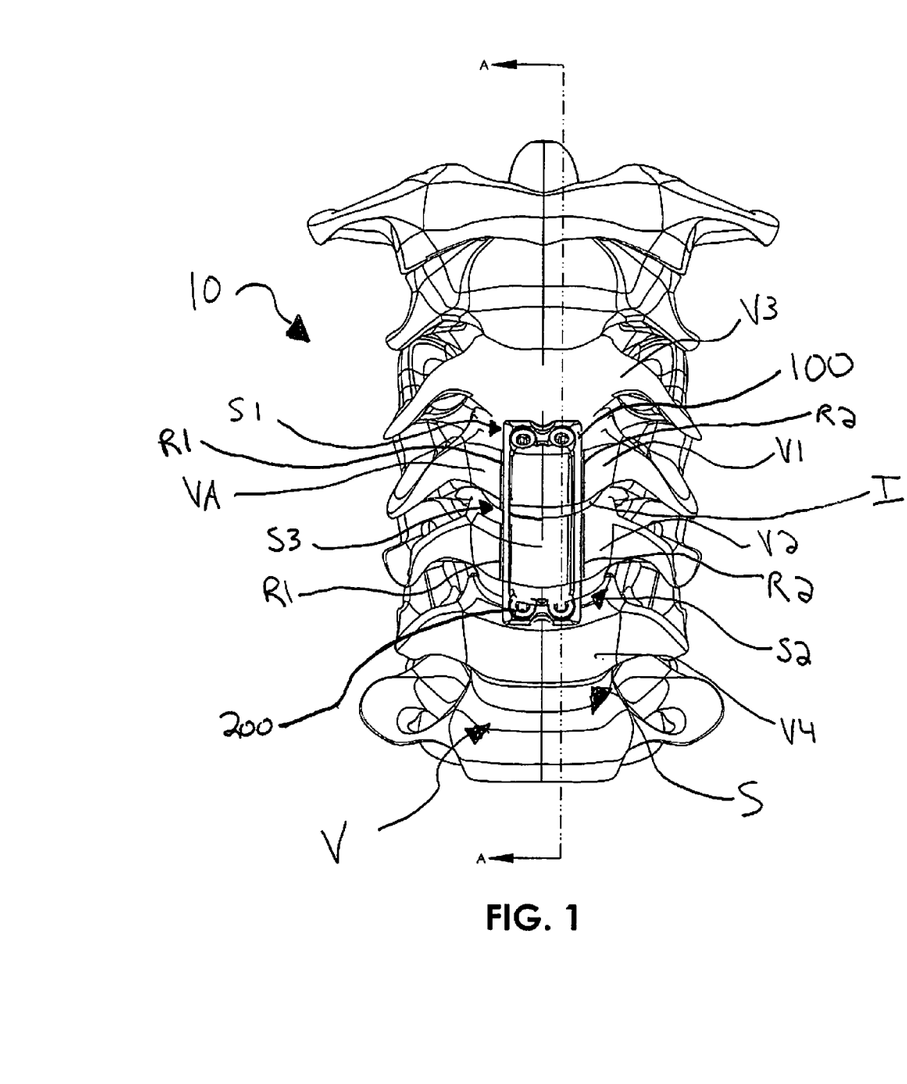
FIG. 1 is a front view of a spinal fixation system shown secured to a spine in accordance with the principles of the present disclosure.

Turning now to FIG. 1, a spinal fixation system is provided in accordance with the present disclosure and is generally identified by reference numeral 10. Spinal fixation system 10 includes a spinal fixation device 100 and a plurality of bone screws 200 for securing the spinal fixation device 100 to a spine in a minimal profile orientation relative to an anterior surface "VA" of one or more vertebrae "V." The bone screws 200 may be formed of a first material such as titanium alloy (e.g., Ti-6AL-4V) and at least a portion of the spinal fixation device 100 may be formed of a second material (e.g., commercially pure titanium). Nonetheless, the first and/or the second material may be formed from any suitable material including, but not limited to, commercially pure titanium, titanium alloys, cobalt chrome alloys, PEEK, stainless steel and the like materials. The first and second materials are selected to enhance securement of the bone screws 200 to the spinal fixation device 100. In this regard, one of the first and second materials may be softer than the other to provide enhanced resistance to backing out of the bone screw 200 from the spinal fixation device 100. One example of this combination of materials is described in U.S. Pat. No. 6,322,562 to Wolter, the entire contents of which are incorporated herein by reference.

With continued reference to FIG. 1, spinal fixation device 100 may be formed as a single, monolithic piece, or may be constructed using any suitable method for joining the components thereof. As will be described in greater detail below, spinal fixation device 100 is configured for positioning at least partially within first and second intervertebral spaces "S1", "S2 and one or more vertebral bodies of the vertebrae "V" of a patient for providing stabilization and support to the spine in a minimal profile orientation. The spinal fixation device 100 may be used to inhibit expulsion of an interbody implant "I" positioned within an intervertebral space "S" such as intervertebral spaces "S1", "S2", and/or "S3."

Figure 2:
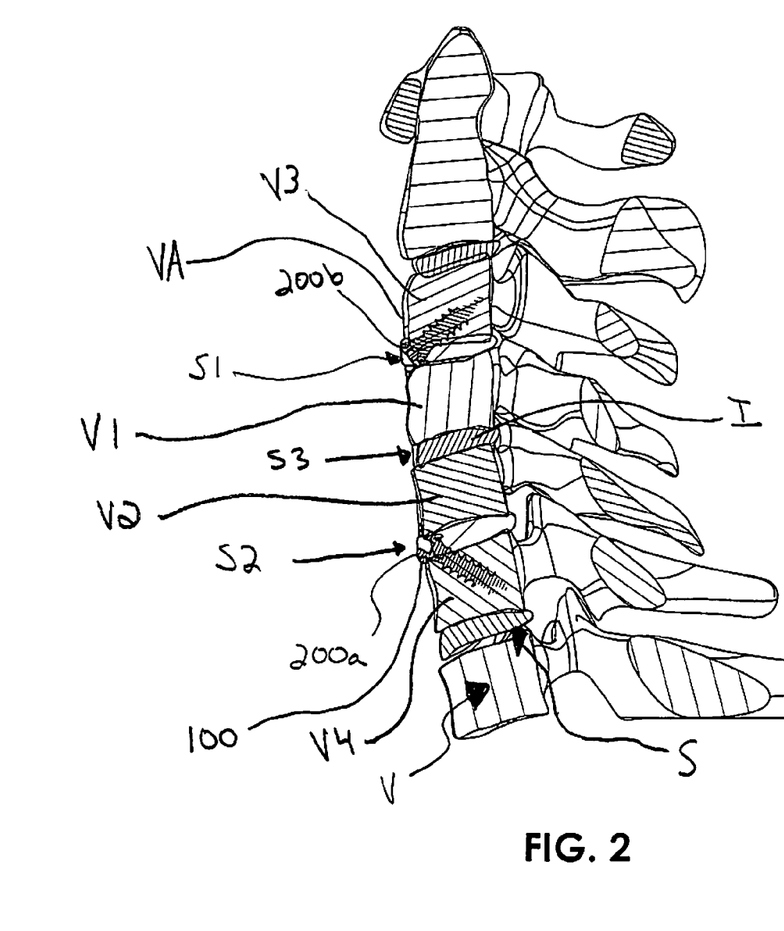
FIG. 2 is a cross-sectional view of FIG. 1 taken along section line A-A.
Figure 3:
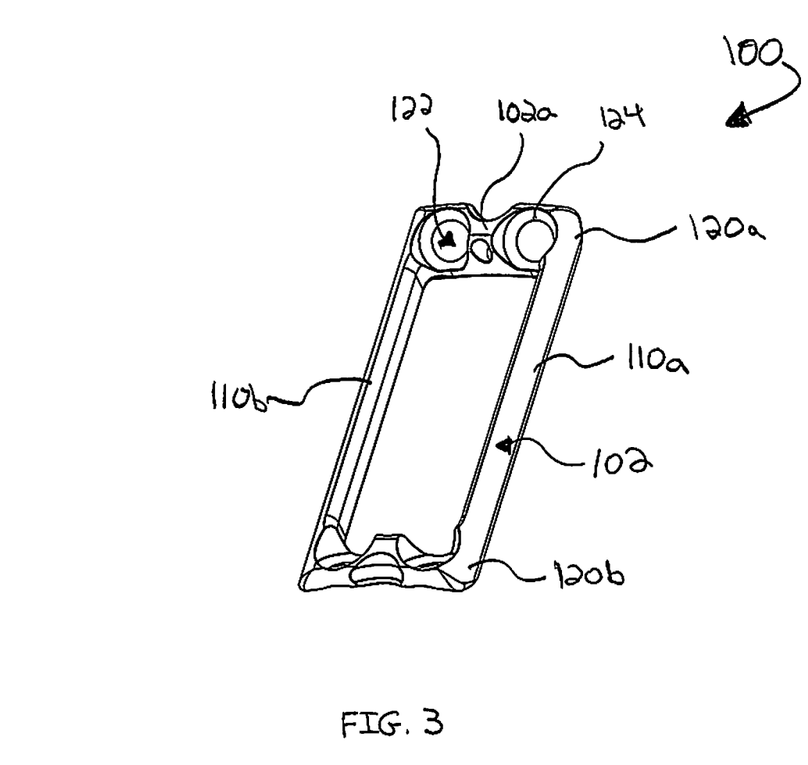
FIG. 3 is a perspective view of a spinal fixation device in accordance with the present disclosure.
Figure 4:
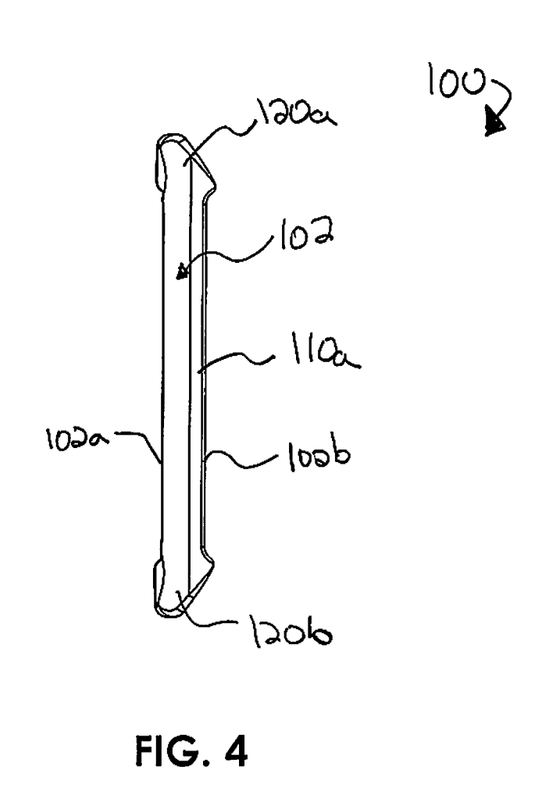
FIG. 4 is a side view of the presently disclosed spinal fixation device of FIG. 3.
Figure 5:
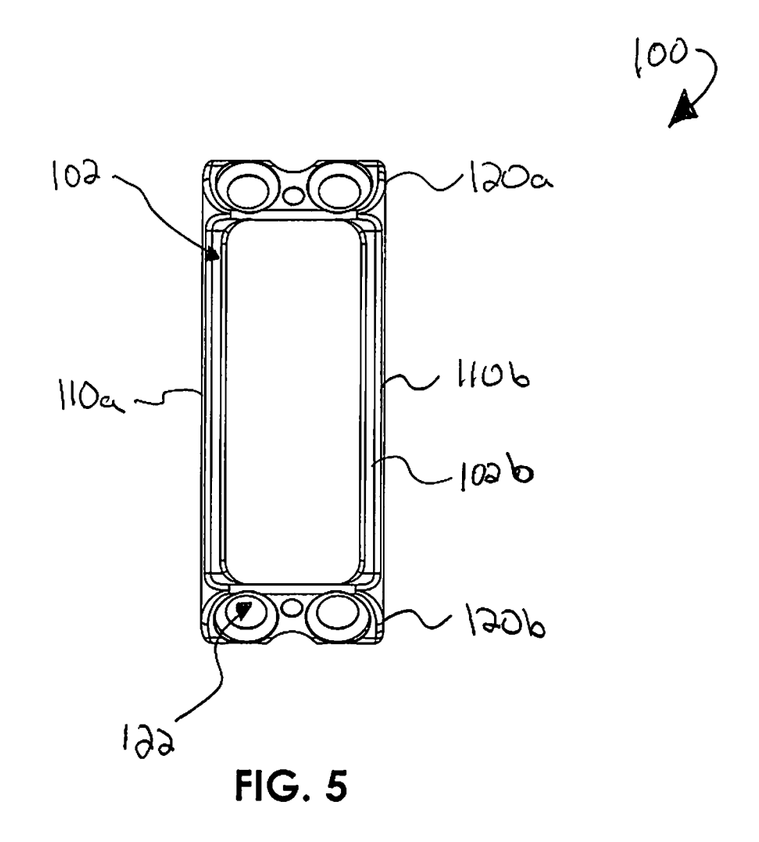
FIG. 5 is a rear view of the presently disclosed spinal fixation device of FIGS. 3 and 4.

Referring now to FIGS. 3-5, spinal fixation device 100 includes a body 102 having an anterior surface 102a and a posterior surface 102b. The body 102 includes a pair of longitudinal members including first and second longitudinal members 110a, 110b extending between a pair of wedge members including first and second wedge members 120a, 120b. The body 102 may be dimensioned to resist deforming forces. More particularly, the first and second longitudinal members 110a, 110b and the first and second wedge members 120a, 120b may have anterior-posterior dimensions in excess of medial-lateral dimensions, or vice versa, to optimally dispose the mass of material and efficiently resist one or both of flexion extension forces and axial compression forces extending through the body 102. This optimization of dimensions may alter the inertia of the body 102. With brief reference to FIGS. 1 and 2, the body 102 may be dimensioned to have a low profile orientation or zero profile orientation relative to an anterior surface "VA" of the one or more vertebrae "V" when secured to a spine as will be described in greater detail below.

As best depicted in FIGS. 3 and 5, the first and second wedge members 120a, 120b are disposed on opposite ends of the first and second longitudinal members 110a, 110b. Illustrated in FIG. 1, each of the first and second wedge members 120a, 120b are intradiscal. More specifically, the first wedge member 120a is at least partially positionable within the first intervertebral space "S1" and the second wedge member 120b is at least partially positionable within the second intervertebral space "S2." One or both of the wedge members 120a, 120b may be at least partially wedge shaped, as viewed in lateral profile best shown in FIG. 4, and may be oriented at any suitable angle and have any suitable dimensions to accommodate various patient geometries and patient dimensions. In embodiments, wedge members 120a, 120b may have any suitable shape (including any suitable geometry and/or dimension) for positioning, at least partially, within one or more of the intervertebral spaces "S." With reference again to FIGS. 3 and 5, each of the first and second wedge members 120a, 120b defines one or more openings 122 therethrough for the reception of the one or more bone screws 200. One or both of the wedge members 120a, 120b may define two or more openings 122 therethrough for the passage and reception of a bone screw 200 in each opening. The openings 122 are disposed at an angle relative to an anterior surface 102a and/or posterior surface 102b of the body 102 and include a lip 124 in order to facilitate the securement of a bone screw 200 to another vertebra adjacent one of the first or second intervertebral spaces "S1", "S2." For example, as illustrated in FIGS. 1 and 2, a first bone screw 200a secures the first wedge member 120a to adjacent vertebra "V3" when the first wedge member 120a is positioned in intervertebral space "S1." Similarly, a second bone screw 200b secures the second wedge member 120b to adjacent vertebra "V4" when the second wedge member 120b is positioned in intervertebral space "S2." As best depicted in FIG. 2, the first and second bone screws 200a, 200b are positioned at an angle commensurate with the angle of the openings 122. The openings 122 may be positioned at any suitable angle to accommodate various dimensions and geometries of the vertebrae of various patients. In this regard, the bone screws 200, when inserted into the openings 122, engage the spinal fixation device 100 to secure the spinal fixation device 100 to the spine.

Illustrated best in FIG. 1, the first and second longitudinal members 110a, 110b define a length that intraosseously spans one or more vertebra "V" of the spine and may have any suitable dimension and/or geometry (including differing dimensions and/or geometries along the length of one or both of the first and second longitudinal members 110a, 110b). In FIG. 1, the first and second longitudinal members 110a, 110b are shown spanning first and second vertebrae "V1", "V2" and intervertebral space "S3" while the first and second wedge members 120a, 120b are secured in the first and second intervertebral spaces "S1", "S2." The first and second longitudinal members 110a, 110b are positioned within a first recess "R1" and a second recess "R2" defined within the first and second vertebrae "V1", "V2." The first and second recesses "R1", "R2" may be cut longitudinally along a path having dimensions and/or geometry sufficient to accommodate one of the first and second longitudinal members 110a, 110b. More particularly, the first and second recess "R1", "R2" may be cut into the vertebral bodies of the first and second vertebrae "V1", "V2", or any number of vertebrae "V" (including a single vertebra "V") commensurate with the dimensions (e.g., length, width, height, etc.) and/or geometry of the first and/or second longitudinal members 110a, 110b, by any suitable bone cutting device such as a jig.

As discussed above, the first and second longitudinal members 110a, 110b are at least partially positionable within the respective first and second recess "R1", "R2" of the one or more vertebra "V" when the first and second wedge members 120a, 120b are positioned within the respective first and second intervertebral spaces "S1", "S2" to maintain the body 102 in a minimal profile orientation (e.g., low or zero profile orientation) relative to the spine. In this regard, the first and second wedge members 120a, 120b are recessed into the first and second intervertebral spaces "S1", "S2" while the first and second longitudinal members 110a, 110b are recessed into the first and second recesses "R1", "R2" to maintain the anterior surface 102a of the body 102 in close relationship, e.g., even with or below (zero profile), or substantially even with (low profile), the anterior surface "VA" of the one or more vertebrae "V." More specifically, a zero profile is achieved when the first and second longitudinal members 110a, 110b (e.g., length and/or width and/or height) are even with (e.g., flush) or below the anterior surface "VA" of the one or more vertebrae "V" along at least a portion of the one or more vertebrae "V." In this respect, the first and second longitudinal members 110a, 110b may be positioned partially/entirely even with or recessed below the anterior surface "VA" of the one or more vertebrae" to have a zero profile orientation. Similarly, a low profile is achieved when the first and second longitudinal members 110a, 110b (e.g., length and/or width and/or height) are substantially even with (e.g., slightly offset from) the anterior surface "VA" of the one or more vertebrae "V" along at least a portion of the one or more vertebrae "V." In this respect, the first and second longitudinal members 110a, 110b may be partially or entirely substantially even with the anterior surface "VA" of the one or more vertebrae" to have a low profile orientation. The low profile orientation may be within millimeters of the anterior surface "VA" of the one or more vertebrae "V."

In operation, an interbody implant "1" may be positioned between adjacent vertebrae "V1" and "V2" of a patient, e.g., during a spinal fusion procedure. Next, one or more jigs or other known bone cutting devices may be used to cut the recesses "R1" and "R2" (low or zero profile) within one or more of the vertebrae "V", depending on the dimensions and/or geometry of the spinal fixation device 100 and the number of vertebrae "V" and/or spinal discs and/or interbody implants which require support. Next, spinal fixation device 100 is inserted from the anterior side of the spine so that the posterior surface 102b of the spinal fixation device 100 is adjacent the anterior surface "VA" of the one or more vertebrae "V" in a low or zero profile orientation. As discussed above, the spinal fixation device 100 may be dimensioned to span across one or more vertebrae "V" (e.g., between two or more intervertebral disc spaces). For example as illustrated in FIGS. 1 and 2, where the spinal fixation 100 spans a pair of adjacent vertebrae "V" (e.g., across three intervertebral disc spaces "S1, "S2", and "S3"), the first and second wedge members 120a, 120b are recessed into the first and second intervertebral spaces "S1", "S2" while the first and second longitudinal members 110a, 110b are recessed into the first and second recesses "R1", "R2." More particularly, the first and second wedge members 120a, 120b may be at least partially disposed into respective intervertebral spaces "S1", "S2" such that each of the first and second wedge members 120a, 120b are substantially abutting respective adjacent vertebrae. The first wedge member 120a may be in abutment with cephalad vertebra "V3" and caudad vertebra "V1" while second wedge member 120b is in abutment with cephalad vertebra "V2" and caudad vertebra "V4." In this manner, the first and second longitudinal members 110a, 110b are recessed into respective recesses "R1", "R2" defined along the vertebrae "V1" and "V2." In one embodiment, where the spinal fixation device 100 is dimensioned to span across a single vertebra, e.g., vertebra V1, and between two intervertebral disc spaces, e.g., intervertebral spaces "S1" and "S3", the first wedge member 120a may be in abutment with cephalad vertebra "V3" and caudad vertebra "V1" while second wedge member 120b is in abutment with cephalad vertebra "V1" and caudad vertebra "V2." In this embodiment, the first and second longitudinal members 110a, 110b are recessed into respective recesses "R1", "R2" defined along the vertebra "V1."

As can be appreciated, the substantially wedge-shaped configuration of first and second wedge members 120a, 120b permits first and second wedge members 120a, 120b to be inserted various distances into the respective intervertebral spaces "S1" and "S2", e.g., to achieve a desired spacing between the respective adjacent vertebrae such as adjacent vertebrae "V3", "V1" and "V2", "V4" and/or to achieve a desired position relative to the interbody implant "I." In particular, where relatively small spacing between the adjacent vertebrae is desired, first and second wedge members 120a, 120b are advanced a relatively short distance into the intervertebral spaces "S." On the other hand, where a relatively larger spacing is desired, first and second wedge members 120a, 120b may be advanced further into the intervertebral spaces "S." The depth of advancement of the first and/or second wedge member 120a, 120b may be commensurate with the depth of the recesses "R1", "R2" to establish a low or zero profile orientation relative to the anterior surface "VA" of one or more vertebrae "V." It is also contemplated that the presently disclosed fixation device 100 may be secured to the spine without an implant "I" positioned in an intervertebral space "S" such as intervertebral space "S3."

Advantageously, because spinal fixation device 100 is not attached to the interbody implant "I", the relative positions of the implant "I" and the spinal fixation device 100 may be adjusted independently of one another (and/or relative to one another). The ability to adjust the relative position of the spinal fixation device 100 relative to the interbody implant "I", and the fact that the fixation device may be disposed partially within and partially outside the two or more intervertebral spaces, e.g., intervertebral spaces "S1" and "S2" advantageously provides the surgeon flexibility with respect to the size and position of the implant "I" that can be placed between the vertebrae "V."

Once spinal fixation device 100 is positioned as desired, a bone screw 200 may be inserted into spinal fixation device 100 though each of the openings 122. For example, two bone screws 200 are advanced through the openings 122 of the first wedge member 120a and then driven into the cephalad vertebra "V3" while two more bone screws 200 are advanced through openings 122 of the second wedge member 120b and driven into the caudad vertebra "V4" so that the spinal fixation device 100 is secured in position. The heads of the bone screws 200 may be configured to deform lips 124 (FIG. 3) of openings 122 to facilitate the securement of the bone screws 200 therein. As can be appreciated, where an interbody implant "I" is inserted, the spinal fixation device 100 inhibits the expulsion of the interbody implant "I" when secured to the spine.

It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

What is claimed is:

1. A spinal fixation device for securing to a spine, comprising:
    a body including at least one longitudinal member extending between a pair of wedge members, each wedge member defining at least one opening therethrough for the reception of a bone screw, the pair of wedge members being disposed on opposite ends of the at least one longitudinal member, one of the wedge members being at least partially positionable within a first intervertebral space of the spine and the other wedge member being at least partially positionable within a second intervertebral space of the spine, the at least one longitudinal member defining a length that spans at least one vertebra of the spine, the pair of wedge members being secured to the at least one longitudinal member such that the at least one longitudinal member is at least partially positioned within the at least one vertebra when the pair of wedge members are positioned within the respective first and second intervertebral spaces to maintain the body in a minimal profile orientation relative to the spine.

2. The spinal fixation device of claim 1, wherein the at least one longitudinal member defines a length that spans a plurality of vertebra of the spine.

3. The spinal fixation device of claim 1, wherein at least one of the pair of wedge members defines at least two openings therethrough for the passage and reception of a bone screw in each opening.

4. The spinal fixation device of claim 1, wherein the at least one opening is disposed at an angle relative to an anterior surface of the body in order to facilitate the securement of the bone screw to another vertebra adjacent one of the first or second intervertebral spaces.

5. The spinal fixation device of claim 1, wherein at least one of the wedge members is at least partially wedge shaped.

6. The spinal fixation device of claim 1, wherein the body is dimensioned to resist deforming forces.

7. The spinal fixation device of claim 6, wherein the body is dimensioned to resist at least one of flexion extension forces and axial compression forces extending through the body.

8. The spinal fixation device of claim 1, wherein the pair of wedge members are secured to the at least one longitudinal member such that the at least one longitudinal member is positioned substantially even with an anterior surface of the at least one vertebra when the pair of wedge members are positioned within the respective first and second intervertebral spaces.

9. The spinal fixation device of claim 1, wherein the pair of wedge members are secured to the at least one longitudinal member such that the at least one longitudinal member is positioned even with an anterior surface of the at least one vertebra when the pair of wedge members are positioned within the respective first and second intervertebral spaces.

10. The spinal fixation device of claim 1, wherein the at least one longitudinal member is positionable within a recess defined within the at least one vertebra.

11. The spinal fixation device of claim 1, wherein the pair of wedge members are secured to the at least one longitudinal member such that the at least one longitudinal member is recessed below an anterior surface of the at least one vertebra when the pair of wedge members are positioned within the respective first and second intervertebral spaces.

12. A system for securing a spinal fixation device to a spine, comprising:
    at least one bone screw;
    a spinal fixation device, comprising:
        a body including a pair of longitudinal members extending between a pair of wedge members, each wedge member defining at least one opening therethrough for the reception of the at least one bone screw, the pair of wedge members being disposed on opposite ends of the pair of longitudinal members, one of the wedge members is at least partially positionable within a first intervertebral space of the spine and the other wedge member is at least partially positionable within a second intervertebral space of the spine, the pair of longitudinal members define a length that spans at least one vertebra of the spine, the pair of wedge members being secured to the pair of longitudinal members such that the pair of longitudinal members is at least partially positioned within the at least one vertebra when the pair of wedge members are positioned within the respective first and second intervertebral spaces to maintain the body in a minimal profile orientation relative to the spine.

13. The system of claim 12, wherein the at least one bone screw is formed of a first material and at least a portion of the spinal fixation device is formed of a second material, the first and second materials being selected to enhance securement of the at least one bone screw to the spinal fixation device.

14. The system of claim 12, wherein the pair of longitudinal members are spaced apart from one another.

15. The system of claim 12, wherein opposite ends of the pair of longitudinal members are connected to opposite ends of the pair of wedge members.

16. The spinal fixation system of claim 12, wherein each wedge member extends to a substantially planar end face that extends from an anterior surface of the body to a posterior surface of the body, the end faces disposed on opposite ends of the body with each end face positioned at an angle oriented in a direction opposite to the other end face, a first one of the wedge members being at least partially positionable within the first intervertebral space so that the end face of the first one of the wedge members engages a first surface of a first vertebral body, the first surface at least partially defining the first intervertebral space, the other wedge member being at least partially positionable within the second intervertebral space so that the end face of the other wedge member engages a second surface of a second vertebral body, the second surface at least partially defining the second intervertebral space.

* * * * *